(12) United States Patent
Bin Muhammad Moizuddin

(10) Patent No.: US 9,657,566 B2
(45) Date of Patent: May 23, 2017

(54) DOWNHOLE TOOL WITH EXPANDER RING

(71) Applicant: HALLIBURTON ENERGY SERVICES, INC., Houston, TX (US)

(72) Inventor: Muhammad Subhan Bin Muhammad Moizuddin, Singapore (SG)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 226 days.

(21) Appl. No.: 14/399,246

(22) PCT Filed: Dec. 31, 2013

(86) PCT No.: PCT/US2013/078399
§ 371 (c)(1),
(2) Date: Nov. 6, 2014

(87) PCT Pub. No.: WO2015/102594
PCT Pub. Date: Jul. 9, 2015

(65) Prior Publication Data
US 2016/0281501 A1  Sep. 29, 2016

(51) Int. Cl.
*E21B 49/10* (2006.01)
*E21B 23/01* (2006.01)
(Continued)

(52) U.S. Cl.
CPC .......... *E21B 49/10* (2013.01); *E21B 17/1014* (2013.01); *E21B 23/01* (2013.01);
(Continued)

(58) Field of Classification Search
CPC .......... G01N 33/24; E21B 7/04; E21B 47/18; E21B 47/024; E21B 43/105; E21B 49/00;
(Continued)

(56) References Cited

U.S. PATENT DOCUMENTS

| 5,092,423 A | 3/1992 | Petermann |
|---|---|---|
| 6,179,066 B1 | 1/2001 | Nasr et al. |

(Continued)

FOREIGN PATENT DOCUMENTS

| EP | 0199503 | 10/1991 |
|---|---|---|
| WO | WO-03/097999 | 11/2003 |

OTHER PUBLICATIONS

PCT International Search Report & Written Opinion, dated Sep. 25, 2014, Appl No. PCT /US2013/078399, "Predicting Temperature-Cycling-Induced Downhole Tool Failure," Filed Dec. 30, 2013, 11 pgs.

*Primary Examiner* — Brad Harcourt
(74) *Attorney, Agent, or Firm* — Iselin Law PLLC; Alan Bryson

(57) ABSTRACT

In at least some embodiments, a downhole tool includes a tool body defining a tool centerline, and a recessed ring guide intermediate to ends of the tool body. The downhole tool also includes an expander ring having an asymmetric wall thickness and rotatable around the recessed ring guide between a reduced tool profile orientation and an expanded tool profile orientation. The downhole tool also includes an actuator configured to rotate the expander ring between the reduced profile orientation and the expanded profile orientation.

20 Claims, 12 Drawing Sheets

(51) Int. Cl.
*E21B 17/10* (2006.01)
*E21B 49/00* (2006.01)
*G01N 33/24* (2006.01)
*E21B 7/04* (2006.01)
*E21B 47/024* (2006.01)
*E21B 47/18* (2012.01)

(52) U.S. Cl.
CPC ............. *E21B 49/00* (2013.01); *G01N 33/24* (2013.01); *E21B 7/04* (2013.01); *E21B 47/024* (2013.01); *E21B 47/18* (2013.01)

(58) Field of Classification Search
CPC ........ E21B 49/086; E21B 49/08; E21B 49/06; E21B 49/02; E21B 49/006; E21B 49/005; E21B 49/10
See application file for complete search history.

(56) References Cited

U.S. PATENT DOCUMENTS

| | | | |
|---|---|---|---|
| 6,805,196 B2* | 10/2004 | Lawrence | B21D 17/04 166/207 |
| 7,900,708 B2 | 3/2011 | Obrejanu | |
| 2003/0098156 A1 | 5/2003 | Follini et al. | |
| 2005/0194127 A1* | 9/2005 | Campo | E21B 43/105 166/207 |
| 2008/0308279 A1 | 12/2008 | Zazovsky et al. | |
| 2008/0314587 A1 | 12/2008 | Del Campo et al. | |
| 2010/0083748 A1 | 4/2010 | Kerr et al. | |
| 2013/0062059 A1 | 3/2013 | Pop et al. | |
| 2013/0081803 A1 | 4/2013 | Tao et al. | |

\* cited by examiner

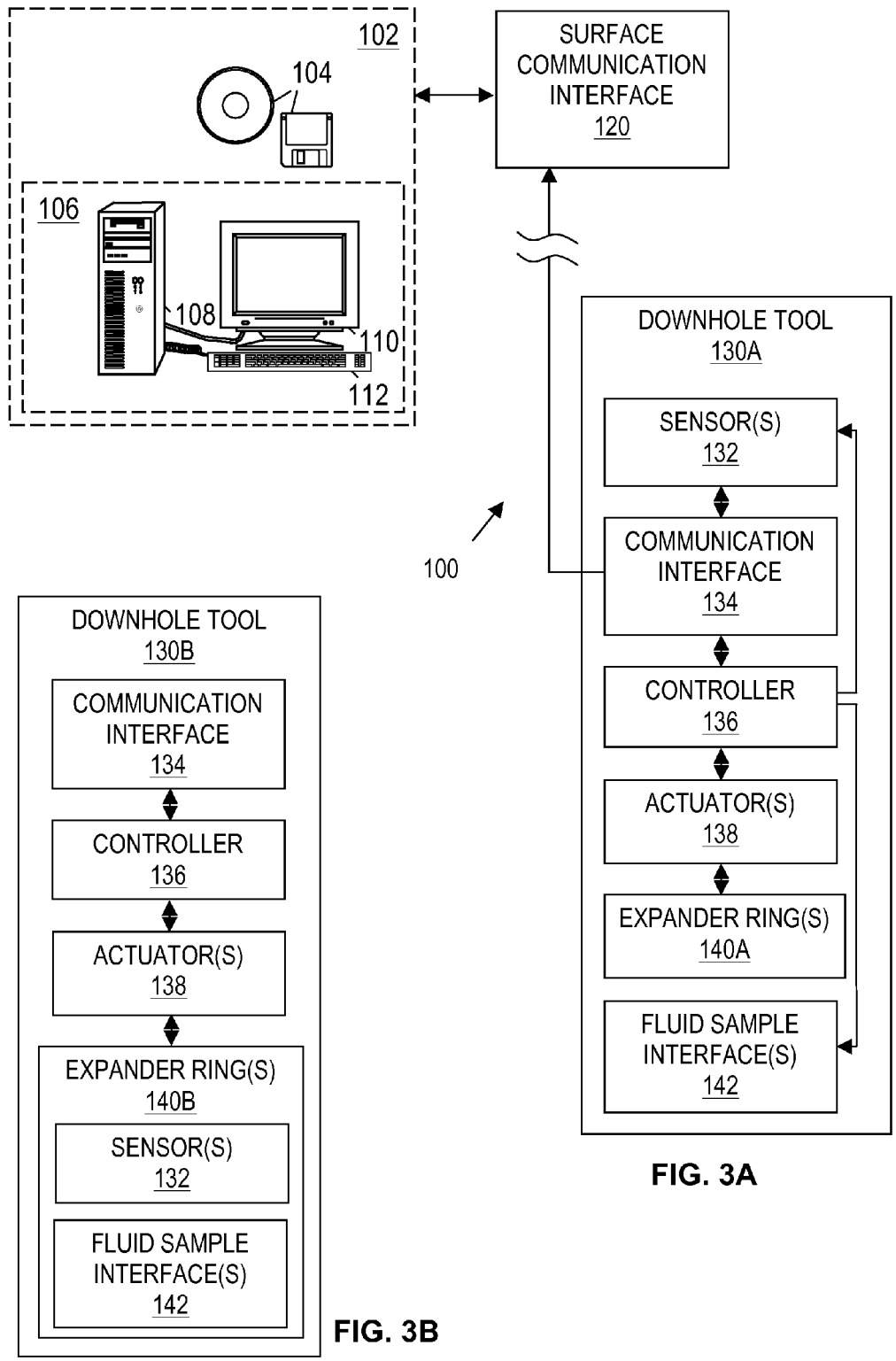

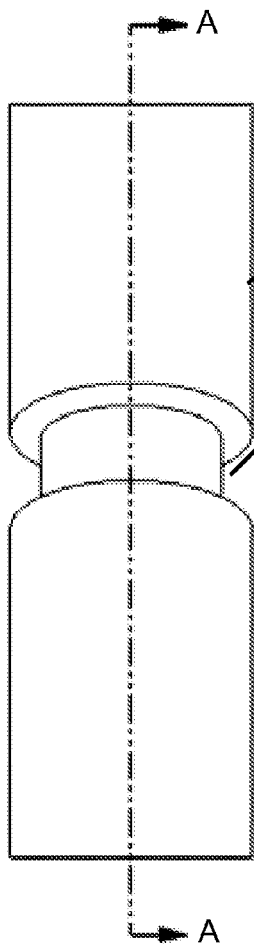
FIG. 4A
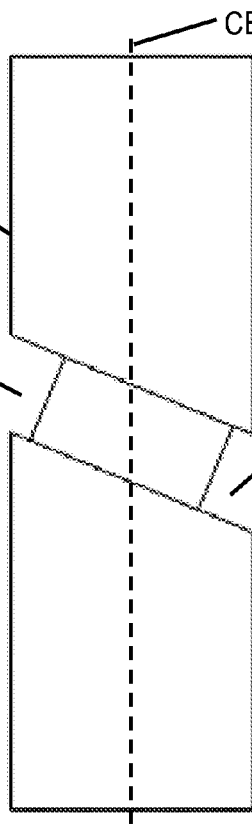
FIG. 4C
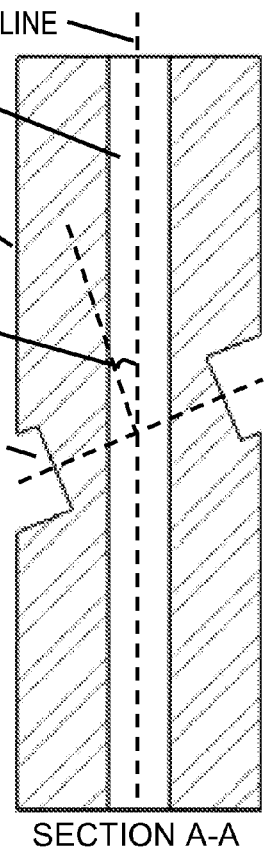
SECTION A-A
FIG. 4E
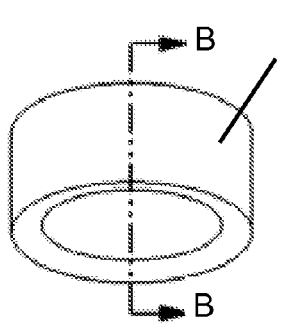
FIG. 4B
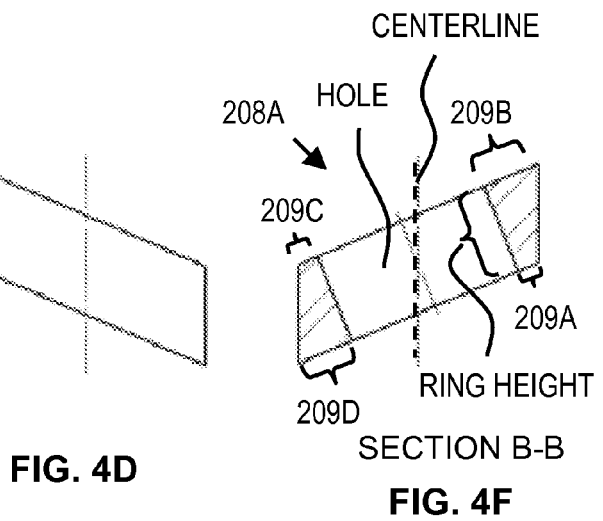
FIG. 4D
SECTION B-B
FIG. 4F

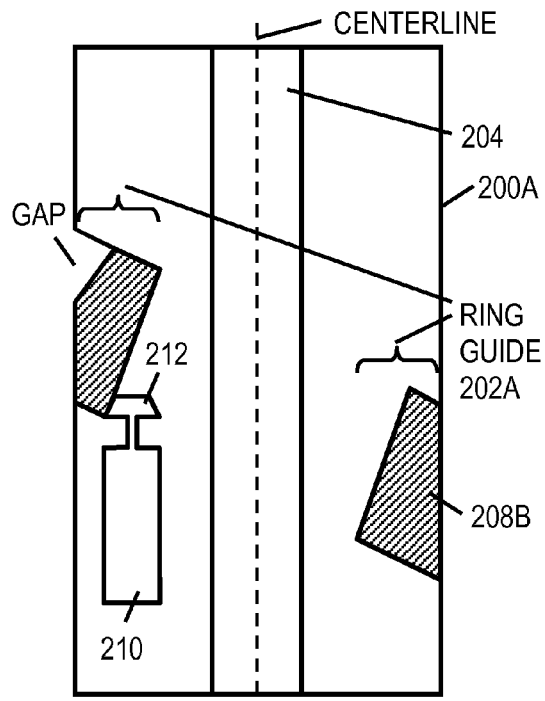
FIG. 5A
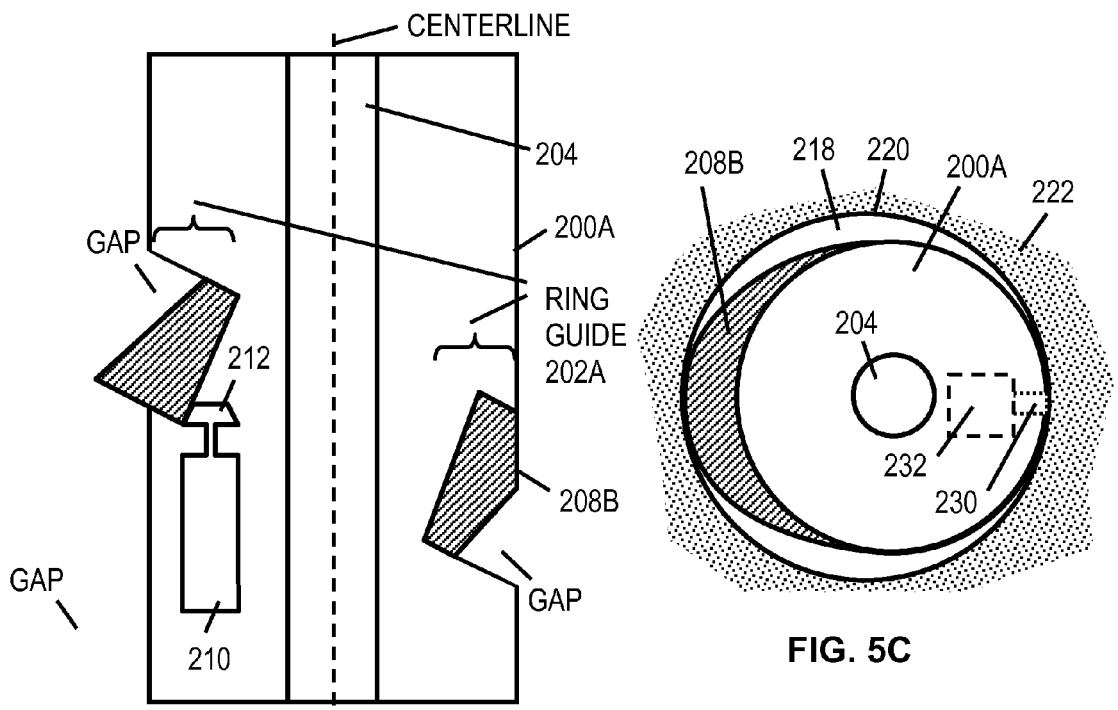
FIG. 5B
FIG. 5C

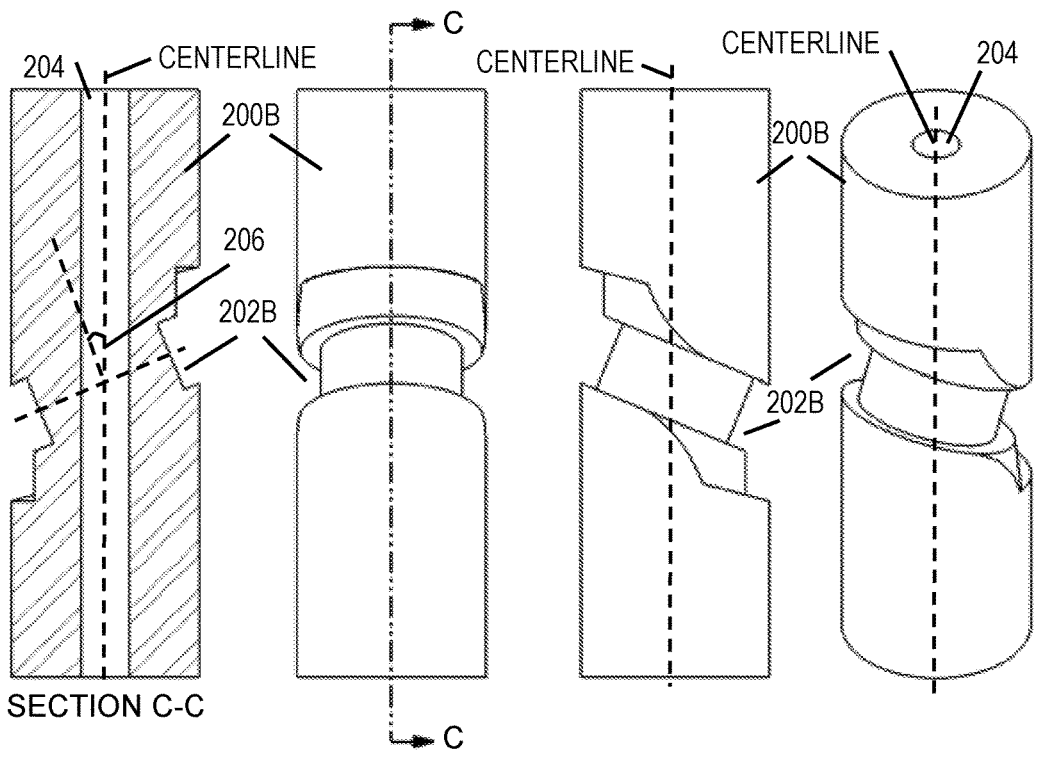
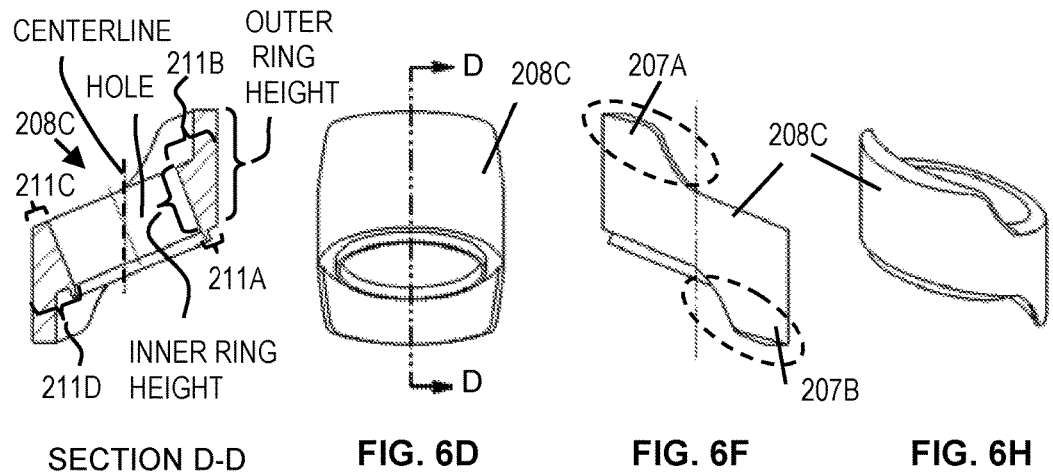
FIG. 6A  FIG. 6C  FIG. 6E  FIG. 6G
FIG. 6B  FIG. 6D  FIG. 6F  FIG. 6H

DOWNHOLE TOOL WITH EXPANDER RING

BACKGROUND

During oil and gas exploration, many types of information are collected and analyzed. The information is used to determine the quantity and quality of hydrocarbons in a reservoir, and to develop or modify strategies for hydrocarbon production. One technique for collecting relevant information involves establishing contact with or increasing proximity to a borehole wall to enable sensor measurements or fluid sampling. The manner in which contact with or proximity to a borehole wall is established is not a trivial issue, and affects tool durability, cost, and complexity.

BRIEF DESCRIPTION OF THE DRAWINGS

Accordingly, there are disclosed herein various methods and systems for providing a downhole tool with an expander ring. In the drawings:

FIGS. 3A and 3B show illustrative components of a downhole tool system.

FIGS. 4A-4J show views of a first illustrative downhole tool configuration.

FIGS. 5A-5C show views of a second illustrative downhole tool configuration.

FIGS. 6A-6J show views of a third illustrative downhole tool configuration.

Figure 1:
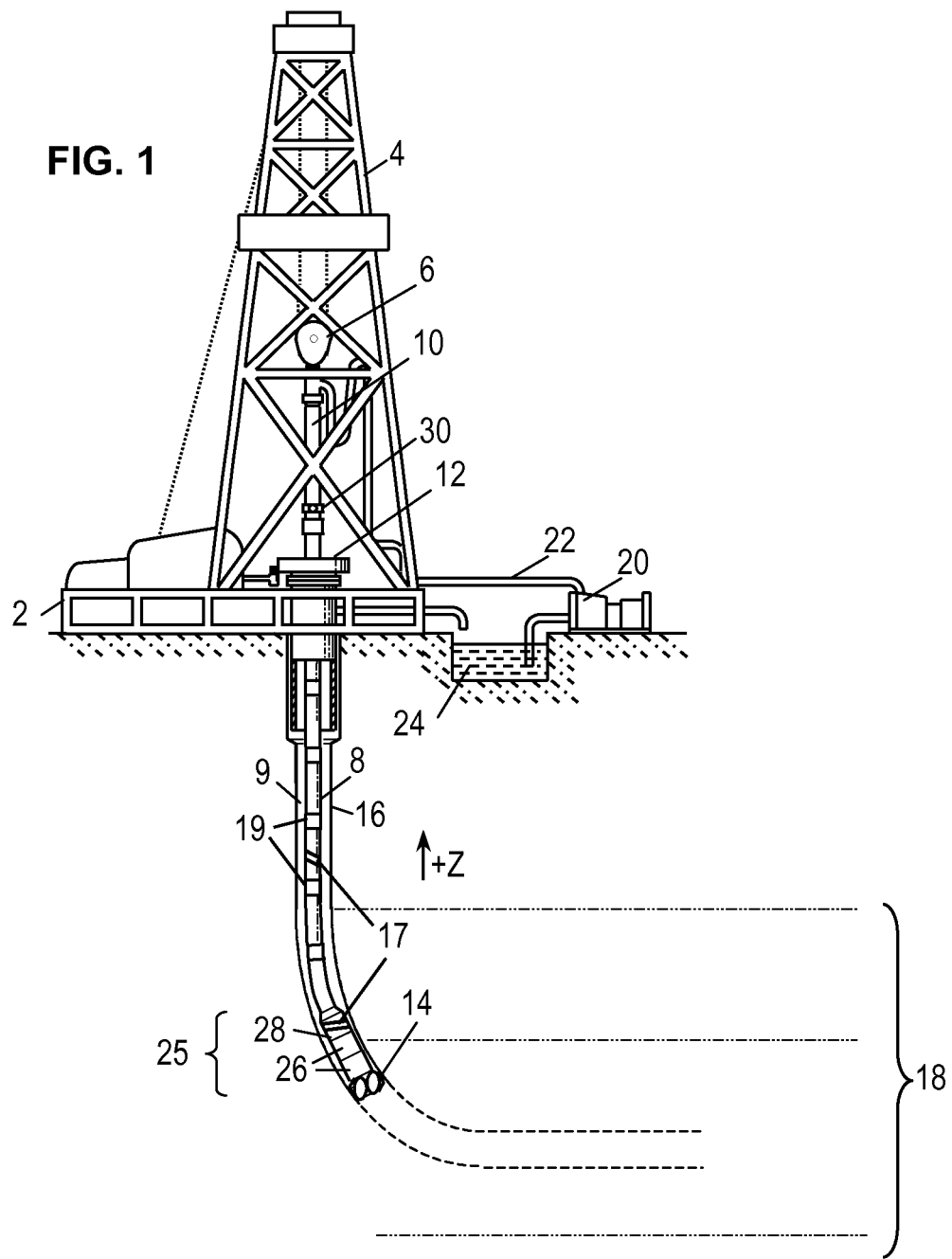
FIG. 1 shows an illustrative drilling environment.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

The following disclosure is directed in part to a downhole tool with one or more expander rings that are selectively rotated to increase an outer tool profile, such as for selectively approaching or engaging a borehole wall for a purpose such as fluid sampling or collecting measurements. After such collection of sensor measurements and/or a fluid sample, the expander ring may be rotated again to reduce the outer tool profile such that the expander ring does not interfere with movement of the downhole tool in the borehole. The downhole tool may then be moved up or down to a new location in the borehole, and the expander ring may again be rotated to increase the outer tool profile to facilitate sensor measurements, fluid sampling, and/or other operations.

In an example embodiment, a downhole tool includes a tool body, which may be substantially circular and may alternatively be referred to as a mandrel. The tool body defines a tool centerline that passes through opposing ends of the tool body. The tool body may be cylindrical such as in the case of a mandrel, but is not required to be so. As such, the tool centerline may either be a straight axis, as in the case of a cylindrical tool body, or a non-linear centerline, such as in the case of an asymmetric part. The tool body includes an intermediate portion between the ends of the tool body. The intermediate portion carries an expander ring and may be referred to accordingly as a ring guide. The ring guide is recessed, at least partially, with respect to the outer tool profile. An "expander ring" encircles the tool body at the ring guide, and is thus carried on the ring guide, such that the expander ring can be rotated to change the outer profile of the downhole tool. The expander ring includes an asymmetric wall thickness defining inner and outer ring profiles, and accordingly, has a wall thickness that varies along a perimeter of the ring. The wall thickness of an expander ring may also vary has a function of height. Typically, inner and outer profiles of the expander ring are not concentric, and one or both of the inner and outer profiles may be non-circular. For example, in one embodiment, the inner profile of the expander ring may be circular, and the outer profile may be eccentric or may be circular but non-concentric with the inner profile of the expander ring. Due to the asymmetric wall thickness, the expander ring can be moved about the ring guide to vary an effective tool profile. In particular, the expander ring may be moved between a reduced tool profile orientation and an expanded tool profile orientation. In the expanded tool profile orientation, at least a portion of the expander ring protrudes or projects beyond the downhole tool's normal outer profile. It should be noted that the expander ring is unitary in that it operates as a single moving part. However, in practice, the expander ring may be manufactured from multiple parts, such as to facilitate assembly about the tool body at the ring guide.

In at least some embodiments, the expander ring has a base ring having the form of an transverse slice from a cylinder with a hole that is perpendicular to the opposing faces of the slice. At least some embodiments build upon this base design with one or more wings that further increase the area of the expanded profile. Some embodiments may alternatively or additionally provide a contact surface that conforms to the shape of a borehole wall when the expander ring is in the expanded profile orientation. Further, some expander ring embodiments may include a toothed surface or other mechanism to facilitate actuation of the expander ring.

The disclosed embodiments can be best appreciated in suitable application contexts such as drilling environments and wireline environments. FIG. 1 shows an illustrative drilling environment having a drilling platform 2 that supports a derrick 4 having a traveling block 6 for raising and lowering a drill string 8. A drill string kelly 10 supports the rest of the drill string 8 as it is lowered through a rotary table 12. The rotary table 12 rotates the drill string 8, thereby turning a drill bit 14. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole 16.

In FIG. 1, sections of the drill string 8 may be fastened together using threaded interfaces and/or joined together by adapters 19 to extend the reach of a bottom-hole assembly 25, which includes drill collars 26 and drill bit 14. The drill collars 26 are thick-walled steel pipe sections that provide weight and rigidity for the drilling process. In some embodiments, the bottom-hole assembly 25 also includes a downhole tool 28 with one or more expander rings 17. As another option, one or more sections of the drill string 8 may include an expander ring 17. The downhole tool 28 (which may be built into the drill collars) gathers measurements of various drilling or formation parameters. The collected measurements may be plotted and used for steering the drill string 8 and/or to analyze formation properties. Additionally or alternatively, the downhole tool 28 collects fluid samples.

In some embodiments, measurements from the sensors of the downhole tool 28 are transferred to the surface using known telemetry technologies or communication links Such telemetry technologies and communication links may be integrated with logging tool 28 and/or other sections of drill string 8. As an example, mud pulse telemetry is one common technique for providing a communications link for transferring logging measurements to a surface receiver 30 and for receiving commands from the surface, but other telemetry techniques such as wired drill pipe can also be used.

Figure 2:
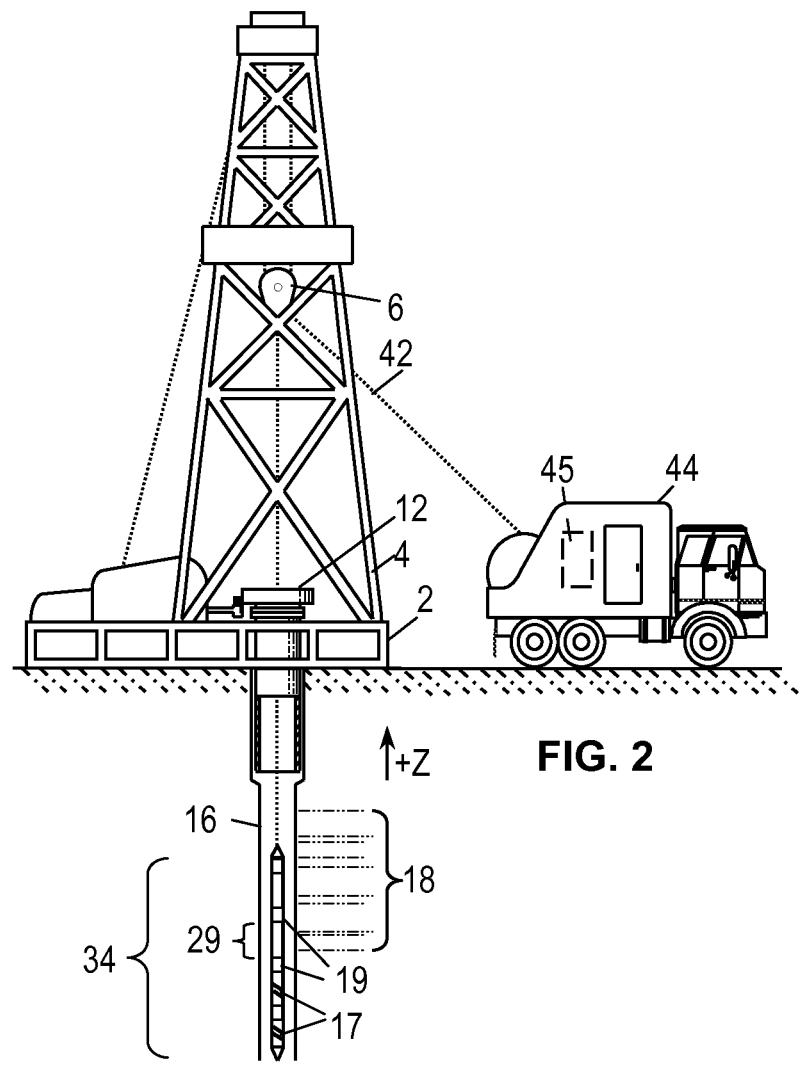
FIG. 2 shows an illustrative wireline environment.

At various times during the drilling process, the drill string 8 shown in FIG. 1 may be removed from the borehole 16. Once the drill string 8 has been removed, as shown in FIG. 2, a wireline tool string 34 can be lowered into the borehole 16 by a cable 42. In some embodiments, the cable 42 includes conductors for transporting power to the tools and telemetry from the tools to the surface. It should be noted that various types of formation property sensors can be included with the wireline tool string 34. As shown, the illustrative wireline tool string 34 includes logging sonde 29 and expander rings 17. The wireline tool string 34 also may include adapters 19 to connect different sections of the wireline tool string together 34.

In FIG. 2, a wireline logging facility 44 collects measurements from the sensors and/or or other instruments in the logging sonde 29. In some embodiments, the wireline logging facility 44 includes computing facilities 45 for managing logging operations, for acquiring and storing measurements gathered by the logging sonde 29, for inverting measurements to determine formation properties, and for displaying the measurements or formation properties to an operator. In different embodiments, the wireline tool string 34 may be lowered into an open section of the borehole 16 or a cased section of the borehole 16.

FIGS. 3A and 3B show illustrative components of a downhole tool system 100. For example, the system 100 may include components of an LWD system or wireline logging system such as those in FIGS. 1 and 2. As shown, the system 100 includes a computer system 102 in communication with a downhole tool 130A via a surface communication interface 120. The downhole tools 130A and 130B of FIGS. 3A and 3B may correspond to the downhole tool 28 of FIG. 1 and/or sections of the wireline tool string 34 of FIG. 2. In system 100, measurements collected by the downhole tool 130A are processed by the computer system 102. The computer system 102 may correspond to, e.g., an onsite facility such as computing facilities 45, or a remote computing system that receives measurements from such facilities. The computer system 102 may include wired or wireless communication interfaces for receiving measurements from downhole tool 130A. Further, the computer system 102 may provide commands or instructions to the downhole tool 130A.

As shown, the illustrative computer system 102 comprises a user workstation 106 with a computer chassis 108 coupled to a display device 110 and a user input device 112. The display device 110 and user input device 112 enable an operator, for example, to interact with software executed by the workstation 106. In at least some embodiments, the computer chassis 108 includes one or more information storage devices 104 for accessing related software. Without limitation, the information storage devices 104 are shown in FIG. 3A in the form of removable, non-transitory information storage media (e.g., optical media disks, drives, etc.). Such software may also be downloadable software accessed through a network such as the Internet). Of course, the computer system 102 also includes one or more processors (not shown) to execute software from storage devices 104 and/or downloaded software.

The downhole tool 130A may correspond to one or more logging while drilling (LWD) or wireline logging tools to collect resistivity/conductivity measurements, delta T sonic measurements, density logs, neutron porosity measurements, gamma ray measurements, repeat formation tests, seismic measurements, pore pressure measurements, compaction trend measurements, fluid samples, overlay calculations, and/or density/sonic crossplots. In at least some embodiments, expander rings 140A of the downhole tool 130A enable corresponding sensors to contact or move closer to the borehole wall. An as example, sensors for resistivity/conductivity, gamma ray, and/or neutron porosity may contact or move closer to the borehole wall when an expander ring is in its expanded profile orientation. In some embodiments, the sensors may be aligned with an outer surface of an expander ring or tool body to enable the sensors to contact or move closer to the borehole wall. Such contact or proximity to the borehole wall can improve the accuracy of the sensor measurements by eliminating or reducing the effect of the mud layer on the measurements. Further, the expander ring can be used to determine a borehole diameter. As an example, the amount of expander ring rotation needed to contact or reach a threshold proximity to the borehole wall can be correlated with a tool diameter and/or borehole diameter. Information regarding the borehole diameter at or near the location of sensors collecting measurements can be used to adjust and otherwise improve the accuracy of the measurements.

The downhole tool 130A also includes a communication interface 134 to send information to surface communication interface 120 and/or to receive information from surface communication interface 120. The communication interface 134 enables measurement data to be transferred to the surface communication interface 120 and the surface computer 102 using known communication techniques (e.g., mud pulse, electromagnetic signaling, or a wired pipe arrangement). It should be understood that the data provided to the surface computer 102 from the downhole tool 130A may include raw measurement data, processed measurement data, inverted measurement data, or other data.

In the system 100, a controller 136 directs various operations of the downhole tool 130A using stored or received instructions. For example, the controller 136 may direct actuator(s) 138 regarding when to rotate the expander ring(s) 140A and the amount of rotation. More specifically, the controller 136 may direct the actuator(s) 138 to independently or simultaneously rotate each of expander ring(s) 140A between a reduced profile orientation and an expanded profile orientation. Further, the controller 136 may direct the operations of sensor(s) 132 and/or fluid sample interface(s) 142.

In accordance with at least some embodiments, the fluid sample interface(s) 142 provides a seal between a borehole wall and the downhole tool 130A when expander ring(s) 140A are in the expanded profile orientation. During the fluid sampling process, fluid is pumped through a flow line until quality of the fluid is determined to above a threshold.

Thereafter, the pumped fluid is stored in a sample chamber for transport to the surface. At least some of the sensor(s) 132 may be employed to monitor properties of the sampled fluid during and/or after the sampling process. Some sensor(s) 132 may additionally or alternatively be employed to collect other types of measurements. For example, the sensor(s) 132 may correspond to seismic sensors that collect measurements while expander ring(s) 140A are in an expanded profile orientation that provides an acoustic coupling between the downhole tool 130A and the borehole wall. Additionally or alternatively, the sensor(s) 132 may correspond to resistivity/conductivity sensors, gamma ray sensors, and/or neutron porosity sensors that collect corresponding measurements while expander ring(s) 140A are in the expanded profile orientation to enable at last some of the sensor(s) 132 to contact or move closer to the borehole wall.

In FIG. 3A, sensor(s) 132 and fluid sample interface(s) 142 are separate from expander ring(s) 140A. Meanwhile, in FIG. 3B, the sensor(s) 132 are integrated with expander ring(s) 140B. For example, the sensor(s) 132 may be embedded in an expander ring or otherwise attached to an expander ring 140B. Additionally or alternatively, fluid sample interface(s) 142 may be integrated with expander ring(s) 140B.

Figure 4G:
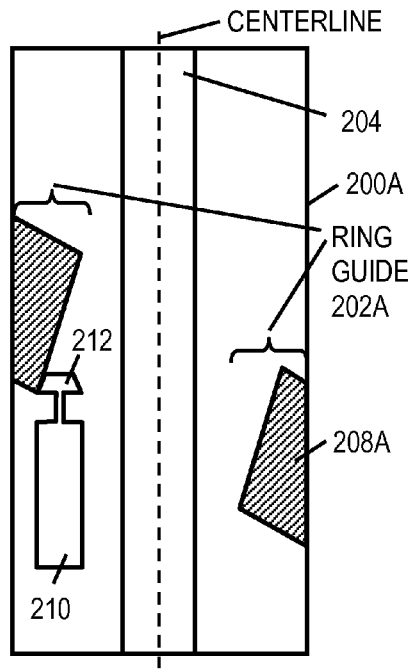

FIGS. 4A-4J show views of a first downhole tool configuration. The downhole tool configuration shown in FIGS. 4A-4J may correspond to, for example, downhole tool 130A or 130B discussed previously. FIGS. 4A and 4C show side views of a downhole tool body 200A with a recessed ring guide 202A. FIG. 4E shows a cross-section of the tool body 200A along the line A-A shown in FIG. 4A. In the cross-section of FIG. 4E, a central passage 204 within the tool body 200A is visible and can be used to channel fluid (e.g., drilling fluid) and/or power/data cables through the tool body 200A. Further, angle 206 is shown and corresponds to an offset angle between the tool centerline of the tool body 200A and the recessed ring guide 202A. In FIGS. 4B, 4D, and 4F, the expander ring 208A is shown. More specifically, FIG. 4B shows an orientation for the expander ring 208A corresponding to the view of FIG. 4A, and FIG. 4D shows an orientation for the expander ring 208A corresponding to the view of FIG. 4C. Meanwhile, FIG. 4F shows a cross-section for the expander ring 208A along the line B-B shown in FIG. 4B. FIG. 4F shows a cross-section for the expander ring 208A along the line B-B shown in FIG. 4B. The orientation in FIG. 4F corresponds to the view of FIG. 4E. As seen best in the cross-section of FIG. 4F, the outer surface of expander ring 208A is a transverse slice from a cylinder with a hole that is perpendicular to the opposing faces of the slice. Further, the wall thickness of the expander ring 208A varies around the perimeter and also as a function of ring height. More specifically, for the expander ring 208A, the wall thickness is thinnest and is approximately the same at the lower right portion 209A and the upper left portion 209C in the cross-section of FIG. 4F. Meanwhile, the wall thickness is thickest and is approximately the same at the upper right portion 209B and the lower left portion 209D. In other embodiments, it should be understood that the wall thickness may vary such that each of the referred to portions 209A-209D is different. For example, the hole through the expander ring 208A may be offset to the left or right relative to the example provided in FIGS. 4B, 4D, and 4F. For example, in some embodiments, at least one of the portions 209A or 209C may form a point or corner due to the offset of the hole relative to the centerline. Further, the angle and dimensions of the hole forming the inner profile of the expander ring 208A may vary. Likewise, the ring height and the wall shape may vary.

Figure 4H:
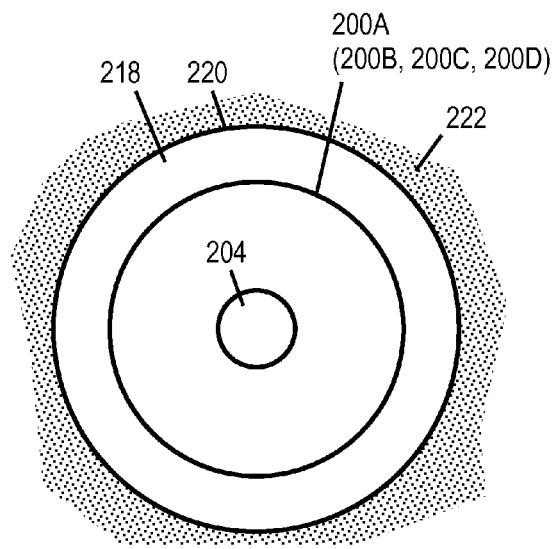

FIG. 4G shows a cross-section along the tool centerline of the tool body 200A with the expander ring 208A positioned in recessed ring guide 202A and in its reduced profile orientation. In this reduced profile orientation, the outer surface of the expander ring 208B is flush with the outer surface of the tool body, thus creating a reduced tool profile. As shown in FIG. 4G, a motor 210 and gear interface 212 may be used to actuate rotation of the expander ring 208A from the reduced profile orientation to an expanded profile orientation. In such embodiments, the expander ring 208A includes a toothed surface that contacts the gear interface 212. Alternatively, the expander ring 208A may be actuated by a hydraulic actuator and includes an attachment mechanism to connect, for example, a hydraulic piston to the expander ring 208A. FIG. 4H shows a cross-section of the downhole tool body 200A in borehole 218 of formation 222 along a plane perpendicular to the tool centerline. In FIG. 4H, the expander ring 208A in its reduced profile orientation has a circular profile that matches the profile of tool body 200A. In an alternative embodiment, the expander ring 208A in the reduced profile orientation could have a diameter that is slightly larger or smaller than the profile of tool body 200A. The same or similar profile shown in FIG. 4H may also apply to other embodiments described herein. In other words, tool bodies 200B, 200C, and 200D and their respective expander rings may form a circular profile as shown in FIG. 4H when the expander rings are in their reduced profile orientation. In alternative embodiments, the respective expander rings in the reduced profile orientation could have a diameter that is slightly larger or smaller than the profile of tool bodies 200B, 200C, and 200D.

Figure 4I:
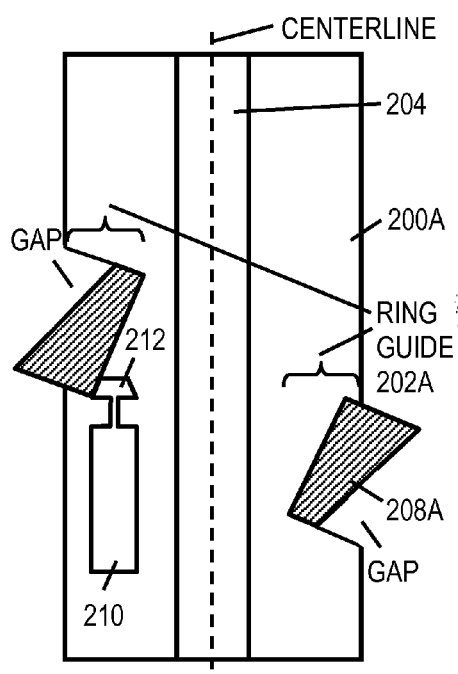
Figure 4J:
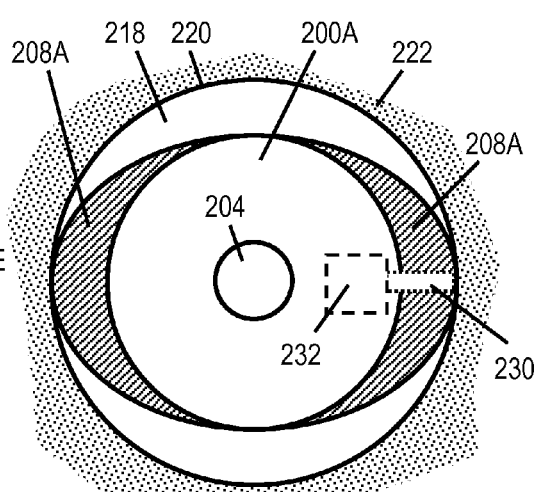

FIG. 4I shows a cross-section along the tool centerline of the tool body 200A with the expander ring 208A in its fully expanded profile. The fully expanded profile is achieved by rotating the expander ring 208A 180 degrees from the reduced profile orientation around recessed ring guide 202A. As shown in FIG. 4I, part of the space corresponding to the recessed ring guide 202A is unoccupied (gaps are present) when the expander ring 208A is in its fully expanded profile. Further, in FIG. 4I, the profile of the expander ring 208A projects beyond the sides of the tool body 200A. FIG. 4J shows a cross-section of the downhole tool body 200A in borehole 218 of formation 222 along a plane perpendicular to the tool centerline with the expander ring 208A in an expanded profile orientation. In FIG. 4J, the expanded profile of the expander ring 208A relative to borehole 218 is visible. More specifically, the expander ring 208A extends beyond the normal tool profile to create an expanded profile that has been broadened in two directions.

In FIG. 4J, the expander ring 208A in its fully expanded profile may be proximate to or contact the wall 220 of borehole 218 in two areas. It should be understood that the expander ring 208A may be proximate to or contact the borehole wall 220 before reaching the fully expanded profile. Depending on the particular application, expander ring 208A in an expanded profile orientation may serve to anchor the tool in place, to center the tool in the borehole, to enable contact or proximity between a sensor and the borehole wall, to enable contact or proximity between a fluid sample interface and the borehole wall, and/or to bridge the gap between the tool and the borehole wall. Once the expander ring 208A contacts or is proximate to the borehole wall 220, sensor measurements and/or fluid samples are collected. In some embodiments, the expander ring 208A may include a fluid sampling interface 230 and/or sensors 232. Once sensor measurements and/or fluid samples are collected, the motor 210 and gear interface 212 are actuated again to return the expander ring 208A to its reduced profile orientation.

FIGS. 5A-5C show views of a second downhole tool configuration. The downhole tool configuration shown in FIGS. 5A-5C may correspond to, for example, downhole tool 130A or 130B discussed previously. FIG. 5A shows a cross-section along the tool centerline of tool body 200A with expander ring 208B positioned in recessed ring guide 202A and in its reduced profile orientation. As shown in FIG. 5A, part of the space corresponding to the recessed ring guide 202A is unoccupied when the expander ring 208B is in its reduced profile orientation (a gap is present). The expander ring 208B is much like the ring of FIGS. 4A-4J, but with one wing or section removed to maintain a circular profile on one side of the tool when the expander ring 208B is in its expanded profile orientation. Removal of the wing or section also may increase the contact area or area of proximity between the expander ring 208B in its expanded profile orientation and a borehole wall. As previously described for expander ring 208A, a motor, gear interface, toothed surfaces, hydraulic actuator, piston, and/or other actuation elements may be employed to rotate expander ring 208B around the recessed ring guide 202A. Further, the tool body 200A and expander ring 208B may form a circular profile as shown in FIG. 4H when the expander ring 208B is in its reduced profile orientation.

FIG. 5B shows a cross-section along the centerline of the tool body 200A with the expander ring 208B in its fully expanded profile. As shown in FIG. 5B, more of the recessed ring guide 202B is unoccupied (compare with FIG. 5A) when the expander ring 208B is in its fully expanded profile (the gaps are larger). Further, in FIG. 5B, the profile of the expander ring 208C projects beyond one side of the tool body 200A. FIG. 5C shows a cross-section of the downhole tool body 200A in borehole 218 of formation 222 along a plane perpendicular to the tool centerline with the expander ring 208B in an expanded profile orientation. As shown, the expander ring 208B projects beyond the normal tool profile to create an expanded profile that has been broadened in one direction. The fully expanded profile is achieved by rotating the expander ring 208B 180 degrees from the reduced profile orientation around recessed ring guide 202A.

In FIG. 5C, the expander ring 208B in its fully expanded profile contacts or is proximate to the wall 220 of borehole 218 in one area. It should be understood that the expander ring 208B may be proximate to or contact the borehole wall 220 before reaching the fully expanded profile. Once the expander ring 208B is close to (within a threshold proximity) or contacts the borehole wall 220, sensor measurements and/or fluid samples are collected. For example, the expander ring 208B may include a fluid sampling interface and/or sensors as described for other expander rings. Alternatively, the expander ring 208B may enable the tool body 200A to contact or move proximate to the borehole wall 220 to facilitate fluid sampling and/or sensor measurements. For example, sensors 232 and/or a fluid sample interface 230 may be part of the tool body 200A, and are optionally in the expander ring 208B. Once sensor measurements and/or fluid samples are collected, the motor 210 and gear interface 212 are actuated again to return the expander ring 208B to its reduced profile orientation.

Figure 6I:
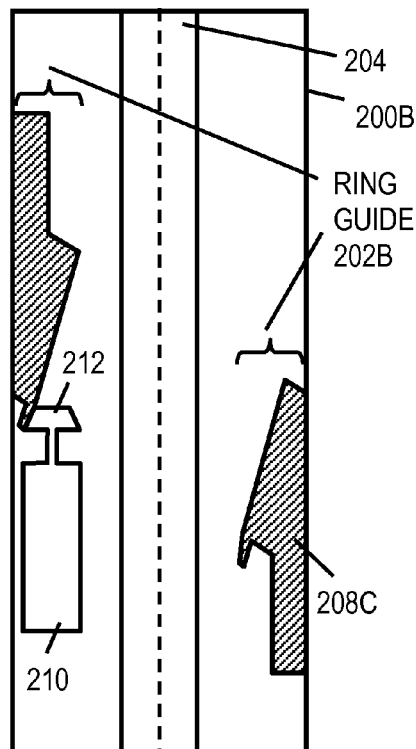

FIGS. 6A-6J show views of a third downhole tool configuration. The downhole tool configuration shown in FIGS. 6A-6J may correspond to, for example, downhole tools 130A or 130B discussed previously. FIGS. 6C and 6E show different side views (a difference of 90 degrees) of a downhole tool body 200B with a recessed ring guide 202B. Meanwhile, FIG. 6G shows a perspective view of tool body 200B, and FIG. 6A shows a cross-section of the tool body 200B along the line C-C shown in FIG. 6C. In the cross-section of FIG. 6A, interior space 204 within the tool body 200B is visible and can be used to channel fluid (e.g., drilling fluid) and/or power/data cables through the tool body 20B. Further, angle 206 is shown and corresponds to an offset angle between the tool centerline of the tool body 200B and the recessed ring guide 202B. In FIGS. 6B, 6D, 6F, and 6H, an expander ring 208C is shown. More specifically, FIG. 6B shows a cross-section for the expander ring 208C along the line D-D shown in FIG. 6D. Further, FIG. 6D shows a side view of the expander ring 208C corresponding to the view of tool body 200B in FIG. 6C, and FIG. 6H shows a perspective view of the expander ring 208C corresponding to the view of tool body 200B in FIG. 6G. Further, FIG. 6F shows a side view of the expander ring 208C corresponding to the view of tool body 200B in FIG. 6E. As shown in FIGS. 6B, 6D, 6F, and 6H, the outer surface of the expander ring 208C is a transverse slice from a cylinder with a hole that is perpendicular to the opposing faces of the slice and with extension members 207A and 207B. The extension members 207A and 207B serve to increase the outer ring height relative to the inner ring height. In other words, the outer profile dimensions are longer in the direction of the centerline than the inner profile dimensions for expander ring 208C. In different expander ring embodiments, the slice angle and the shape/size of the extension members 207A and 207B may vary.

As seen best in the cross-section of FIG. 6B, the wall thickness of the expander ring 208C varies around the perimeter and also as a function of ring height. More specifically, for the expander ring 208C, the wall thickness is thinnest and is approximately the same at the lower right portion 211A and the upper left portion 211C in the cross-section of FIG. 6B. Meanwhile, the wall thickness is thickest and is approximately the same at the upper right portion 211B and the lower left portion 211D. In other embodiments, it should be understood that the wall thickness may vary such that each of the referred to portions 211A-211D is different. For example, the hole through the expander ring 208C may be offset to the left or right relative to the example shown in FIGS. 6B, 6D, 6F, and 6H. For example, in some embodiments, at least one of the portions 211A or 211C may form a point or corner due to the offset of the hole relative to the tool centerline. Further, the angle and dimensions of the hole forming the inner profile of the expander ring 208C may vary. Likewise, the inner ring height, the outer ring height, and the wall shape may vary.

FIG. 6I shows a cross-section along the centerline of the tool body 200B with the expander ring 208C positioned in recessed ring guide 202B and in its reduced profile orientation. As shown, the expander ring 208C and the recessed ring guide 202B may be shaped so that no gaps or spaces are visible while the expander ring 208C is in its reduced profile orientation (a flush fit). As previously described for expander ring 208A, a motor, gear interface, toothed surfaces, hydraulic actuator, piston, and/or other actuation elements may be employed to rotate expander ring 208C around the recessed ring guide 202B. Further, the tool body 200B and expander ring 208C may form a circular profile as shown in FIG. 4H when the expander ring 208C is in its reduced profile orientation.

Figure 6J:
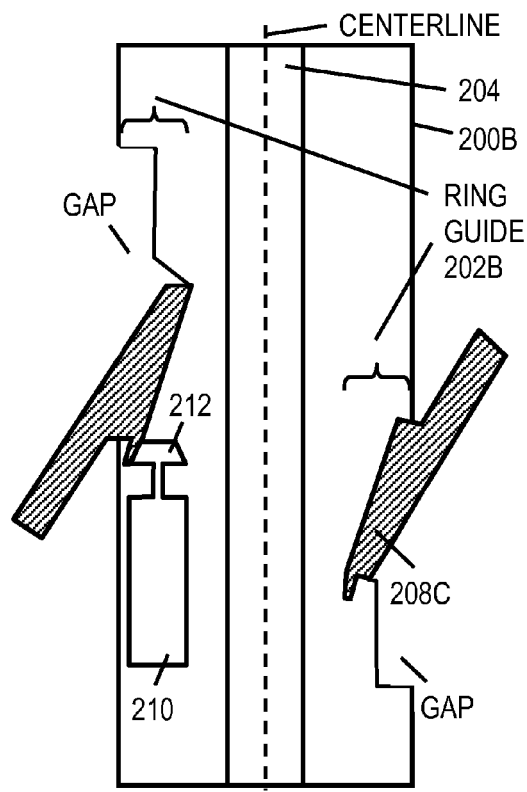

FIG. 6J shows a cross-section along the centerline of the tool body 200B with the expander ring 208C in its fully expanded profile. As shown in FIG. 6J, the recessed ring guide 202B is partially unoccupied when the expander ring 208C is in its fully expanded profile (gaps are present). Further, in FIG. 6J, the profile of the expander ring 208C projects beyond the sides of the tool body 200B. In its expanded profile orientation, the expander ring 208C extends beyond the normal tool profile to create an expanded profile that has been broadened in two directions similar to the profile shown in FIG. 4J. In at least some embodiments, the expander ring 208C projects further beyond the normal tool profile, compared to the expander ring 208A, due to the extension members 207A and 207B. Further, sensors and/or a fluid sampling interface may be integrated with the expander ring 208C as discussed previously for expander ring 208A.

Figure 7A:
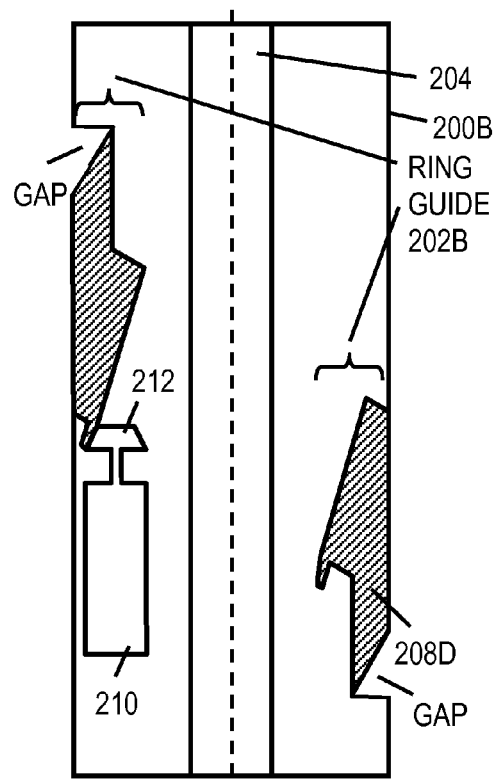
FIGS. 7A and 7B show views of a fourth illustrative downhole tool configuration.
Figure 7B:
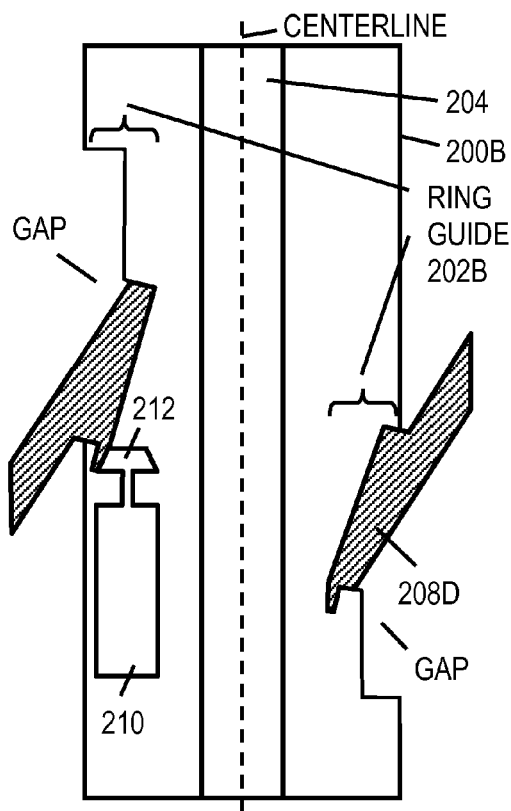

FIGS. 7A and 7B show views of a fourth downhole tool configuration. The downhole tool configuration shown in FIGS. 7A-7B may correspond to, for example, downhole tool 130A or 130B discussed previously. FIG. 7A shows a cross-section along the centerline of tool body 200B with another expander ring 208D positioned in recessed ring guide 202B and in its reduced profile orientation. As shown, part of the recessed ring guide 202B is unoccupied when the expander ring 208D is in its reduced profile orientation. As previously described for expander ring 208A, a motor, gear interface, toothed surfaces, hydraulic actuator, piston, and/or other actuation elements may be employed to rotate expander ring 208D around the recessed ring guide 202B. Further, the tool body 200B and expander ring 208D may form a circular profile as shown in FIG. 4H when the expander ring 208D is in its reduced profile orientation.

FIG. 7B shows a cross-section along the centerline of the tool body 200B with the expander ring 208D in its fully expanded profile. As shown in FIG. 7B, more of the recessed ring guide 202B is unoccupied (compare with FIG. 7A) when the expander ring 208D is in its fully expanded profile (the gaps are larger). Further, in FIG. 7B, the profile of the expander ring 208D projects beyond the sides of the tool body 200B. In its expanded profile orientation, the expander ring 208D extends beyond the normal tool profile to create an expanded profile that has been broadened in two directions similar to the profile shown in FIG. 4J. In FIG. 7B, the expander ring 208D in its fully expanded profile contacts or moves proximate to the wall 220 of borehole 218 in two areas, where the contact area or area of proximity is increased compared to the expander rings 208A and 208C. Further, sensors and/or a fluid sampling interface may be integrated with the expander ring 208D as discussed previously for expander ring 208A.

Figure 8A:
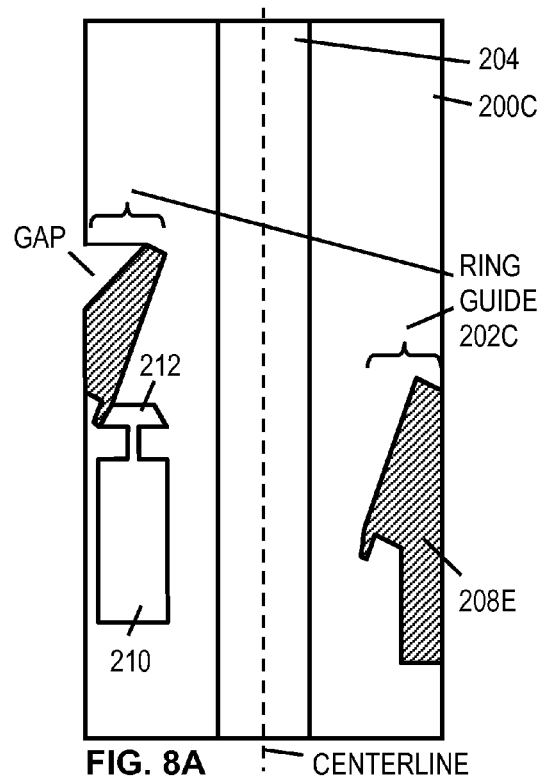
FIGS. 8A and 8B show views of a fifth illustrative downhole tool configuration.
Figure 8B:
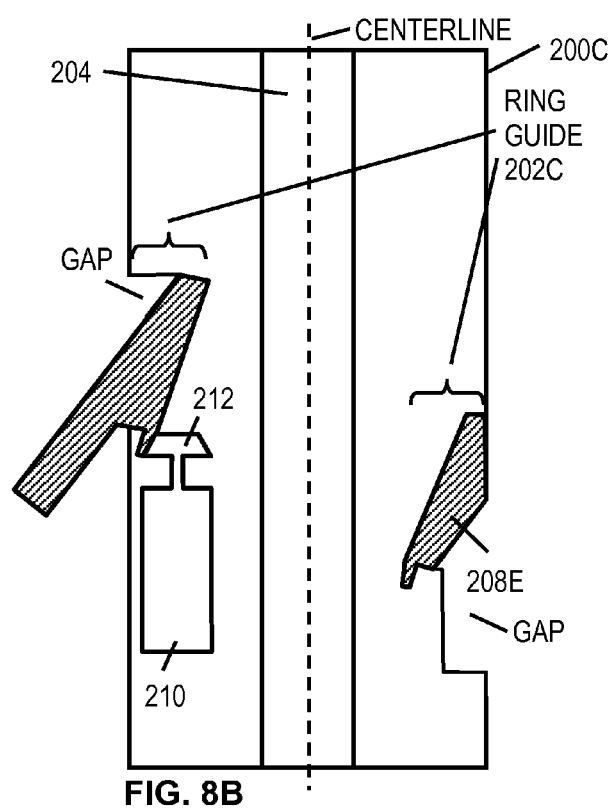

FIGS. 8A and 8B show views of a fifth downhole tool configuration. The downhole tool configuration shown in FIGS. 8A and 8B may correspond to, for example, downhole tool 130A or 130B discussed previously. FIG. 8A shows a cross-section along the centerline of tool body 200C with expander ring 208E positioned in recessed ring guide 202C and in its reduced profile orientation. As shown, the shape of the recessed ring guide 202C is non-symmetric and remains partly unoccupied when the expander ring 208E is in its reduced profile orientation. As previously described for expander ring 208A, a motor, gear interface, toothed surfaces, hydraulic actuator, piston, and/or other actuation elements may be employed to rotate expander ring 208E around the recessed ring guide 202C. Further, the tool body 200C and expander ring 208E may form a circular profile as shown in FIG. 4H when the expander ring 208E is in its reduced profile orientation.

FIG. 8B shows a cross-section along the centerline of the tool body 200C with the expander ring 208E in its fully expanded profile. As shown in FIG. 8B, more of the recessed ring guide 202C is unoccupied (compare with FIG. 8A) when the expander ring 208E is in its fully expanded profile (the gaps are larger). Further, in FIG. 8B, the profile of the expander ring 208E projects beyond one side of the tool body 200C. In its expanded profile orientation, the expander ring 208E extends beyond the normal tool profile to create an expanded profile that has been broadened in one direction similar to the profile shown in FIG. 5C. In at least some embodiments, the expander ring 208E projects further beyond the normal tool profile, compared to the expander ring 208C, using an extension member. Further, sensors and/or a fluid sampling interface may be integrated with the expander ring 208E as discussed previously for expander ring 208A. Alternatively, sensors and/or a fluid sampling interface may be integrated with the with the tool body 200C as discussed previously for tool body 200A.

Figure 9A:
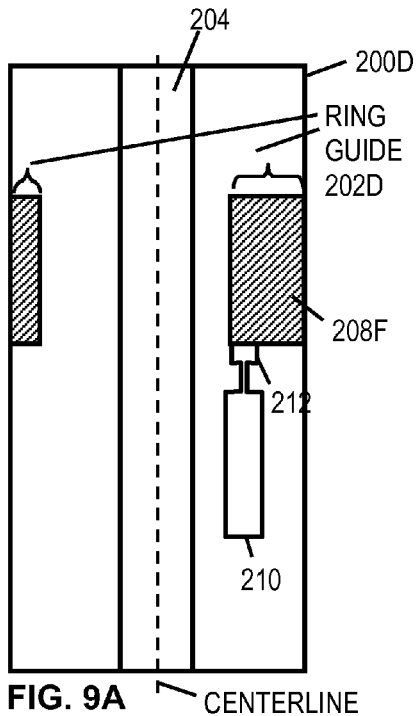
FIGS. 9A-9C show views of a sixth illustrative downhole tool configuration.
Figure 9B:
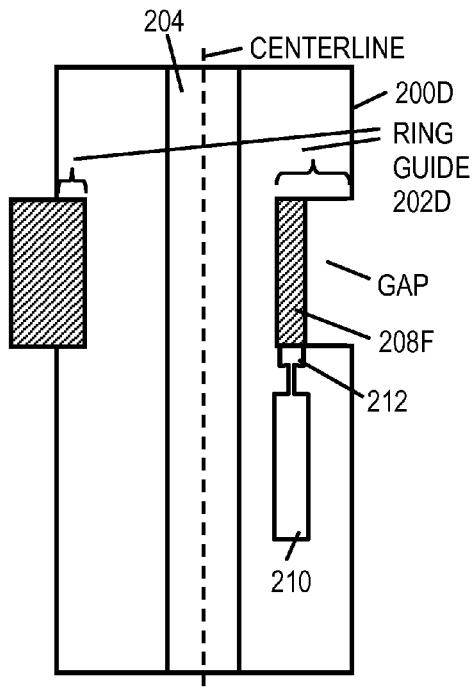
Figure 9C:
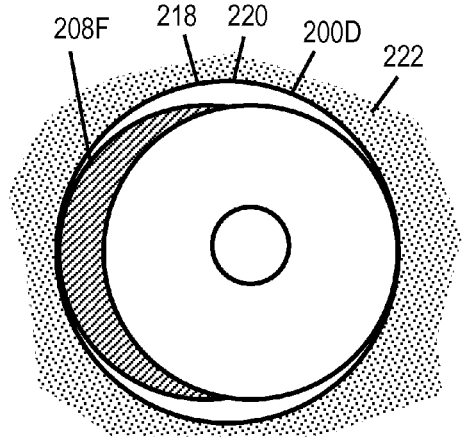

FIGS. 9A-9C show views of a sixth downhole tool configuration. The downhole tool configuration shown in FIGS. 9A-9C may correspond to, for example, downhole tool 130A or 130B discussed previously. FIG. 9A shows a cross-section along the centerline of tool body 200D with expander ring 208F positioned in recessed ring guide 202D and in its reduced profile orientation. As shown, the shape of the recessed ring guide 202C is non-symmetric relative to the tool centerline, and the expander ring 208C may be shaped so that no gaps or spaces are visible while the expander ring 208F is in its reduced profile orientation (a flush fit). As previously described for expander ring 208A, a motor, gear interface, toothed surfaces, hydraulic actuator, piston, and/or other actuation elements may be employed to rotate expander ring 208F around the recessed ring guide 202D. Further, the tool body 200D and expander ring 208F may form a circular profile as shown in FIG. 4H when the expander ring 208F is in its reduced profile orientation.

FIG. 9B shows a cross-section along the centerline of the tool body 200D with the expander ring 208F in its fully expanded profile. As shown in FIG. 9B, part of the recessed ring guide 202D is unoccupied when the expander ring 208F is in its fully expanded profile. Further, in FIG. 9B, the profile of the expander ring 208F projects beyond one side of the tool body 200D.

The fully expanded profile is achieved by rotating the expander ring 208F 180 degrees from the reduced profile orientation around recessed ring guide 202D. FIG. 9C shows a cross-section of the downhole tool body 200D in borehole 218 of formation 222 along a plane perpendicular to the tool centerline with the expander ring 208F in an expanded profile orientation.

In FIG. 9C, the expander ring 208F in its fully expanded profile contacts or moves proximate to the wall 220 of borehole 218 in one area. In its expanded profile orientation, the expander ring 208F extends beyond the normal tool profile to create an expanded profile that has been broadened in one direction similar to the profile shown in FIG. 5C. Further, sensors and/or a fluid sampling interface may be integrated with the expander ring 208F as discussed previously for expander ring 208A. Alternatively, sensors and/or a fluid sampling interface may be integrated with the with the tool body 200D as discussed previously for tool body 200A.

The tool body, recessed ring guide, expander ring, and actuator embodiments described herein are examples only and are not intended to limit downhole tools to a particular configuration. To summarize, the disclosed embodiments describe a downhole tool with a tool body defining a tool centerline and having two ends. The tool centerline may be straight or curved. The tool body includes a recessed ring guide between its ends. The downhole tool also includes an expander ring having an asymmetric wall thickness between an inner profile and outer profile. The expander ring rotates around the recessed ring guide between a reduced profile orientation and an expanded profile orientation, where the expanded profile is larger than the reduced profile and projects beyond the profile of the tool body. The downhole tool also includes an actuator configured to rotate the expander ring between the reduced profile orientation and the expanded profile orientation.

In some embodiments, an expander ring in its reduced profile orientation may align with an outer profile of a downhole tool body. As an example, an expander ring in its reduced profile orientation may have a circular profile that matches the circular profile of the downhole tool in a plane perpendicular to the tool centerline. In other words, the expander ring is fully within the recessed ring guide when in the reduced profile orientation. The expander ring in its expanded profile orientation may have an oval profile or partially oval profile in a plane perpendicular to the tool centerline.

Many different variations for the expander ring and recessed ring guide are possible. For example, in some embodiments, an entire expander ring may project beyond a profile of the tool body when in the expanded profile orientation. In such embodiments, the expander ring rotates around an axle along or beyond the outer surface of the tool body. Further, in different embodiments, an expander ring may rotate at an angle transverse to or perpendicular to the tool centerline. Further, in different embodiments, an expander ring may have a hole that is offset from the tool centerline and/or that is angled relative to the tool centerline. As an example, the expander ring may have a shape corresponding to a transverse slice of a cylinder with a hole that is perpendicular to the slice. Alternatively, the expander ring may have a shape corresponding to a slice of a cylinder with a hole that is offset relative to the tool centerline. When the hole is offset relative to the tool centerline, a slice perpendicular to the tool centerline may be used. In some embodiments, an expander ring may have the shape correspond to a cylinder with a hole and with at least one extension member. As needed, gaps may be employed between a tool body and an expander ring to facilitate assembly and rotation of the expander ring.

Even if an actuation mechanism is not working, an expander ring may rotate from an expanded profile orientation to a reduced profile orientation by contacting the borehole wall during drilling. While only one expander ring is shown in the different example embodiments, it should be that a downhole tool may include multiple expander rings. Each expander ring may be the same or different and may have the same reduced profile orientation and expanded profile orientation. Alternatively, different expander rings of a tool body may have different reduced profile orientations and/or different expanded profile orientations.

In different embodiments, the contact or proximity points between a borehole wall and an expander ring may vary. For example, in some embodiments, an expander ring in the expanded profile orientation contacts or is proximate to a borehole wall on opposite sides of a downhole tool. This can be achieved, for example, by using an expander ring with multiple extension members as described herein. Further, the surface area for each contact or proximity point may be a line or a two-dimensional shape defined by the contact or proximity surface for the expander ring or each extension member. Because the downhole environment is filled with fluids and solids, in some embodiments, an expander ring with a plurality of surfaces, includes elastomer wipers for at least some of the surfaces to keep these surface clean. This reduces the chance of the expander ring jamming from cuttings or other particles in the downhole environments. Further, actuation components or other components related to the expander ring may be isolated from the downhole environment by means of pressure balance seals.

In the expanded profile orientation, an expander ring contacts or moves within a threshold proximity to a borehole wall on only one side of the tool or on multiple sides of the tool. In this manner, sensors and/or a fluid sampling interface may be positioned within a threshold proximity of or contact the borehole wall. Example sensors include seismic sensors, resistivity sensors, gamma ray sensors, and neutron porosity sensors. Such sensors may be integrated with the expander ring and/or may be integrated with a tool body corresponding to the expander ring. In different embodiments, an expander ring may include a fluid sampling interface. The fluid sampling interface includes, for example, a contact surface seal and a flow line that passes inside the expander ring and/or tool body. An expander ring and/or tool body may also include one or more sensors related to fluid sample monitoring or other sense operations. In different embodiments, an expander ring enables acoustic coupling, direct contact, or proximity between sensors and the surrounding formation.

In some embodiments, an interior surface or lip of an expander ring has a toothed surface to mesh with a gear interface. In this manner, a motor with the gear interface is able to mesh with the toothed surface to rotate the expander ring. While the motor is preferably a two-way motor, a one-way motor could be used to rotate an expander ring between its reduced profile orientation and its expanded profile orientation. For a one-way motor to be feasible, the dimensions of the borehole and the expander ring in its expanded profile orientation need to match so that contact with or proximity to the borehole wall does not prevent the expander ring from continuing to rotate (360 degrees from the reduced profile orientation) to return to the reduced profile orientation. Alternatively, an expander ring may be connected to a hydraulic actuator or pump. The hydraulic actuator may include a curved piston, for example, that enables the expander ring to rotate around an expander ring axle up to 180 degrees. To control the rotation of an expander ring between its reduced profile orientation and the expanded profile orientation, sensors or position encoders can be employed. Further, contact sensors or proximity sensors may be employed to indicate when contact with or a threshold proximity to the borehole wall is achieved.

In some situations, an expander ring may fail to return to its reduced profile orientation. Even if an actuation mechanism is not working, an expander ring may rotate from an expanded profile orientation to a reduced profile orientation by contacting the borehole wall during drilling.

Accordingly, in some embodiments, the actuator may include a release mechanism that enables the expander ring to return to its reduced profile orientation by contact with the borehole wall. Further, an expander ring may contact the borehole wall and return to its reduced profile orientation by rotating the drill string (e.g., by drilling). In such case, actuation of the expander ring is not needed, but a release mechanism may be needed.

Further, in some embodiments, redundant actuators may be provided for each expander ring. While only one expander ring is shown in the different example embodiments, it should be noted that a downhole tool may include multiple expander rings. Each expander ring of a downhole tool may be the same or different shape and may have the same reduced profile orientation and expanded profile orientation. Alternatively, different expander rings of a downhole tool may have different reduced profile orientations and/or different expanded profile orientations.

Without limitation, the expander rings described herein may be constructed of metal (e.g., steel), plastic/elastomer (e.g., peek), or a rubber material. To assemble a downhole tool with an expander ring such as those described herein, the expander ring may have two or more parts that are fastened together and put in place in its corresponding expander ring slot. An alternative assembly technique would be to use a tool body having two or more parts that are fastened together once an expander ring is put in place in its corresponding ring slot.

Figure 10:
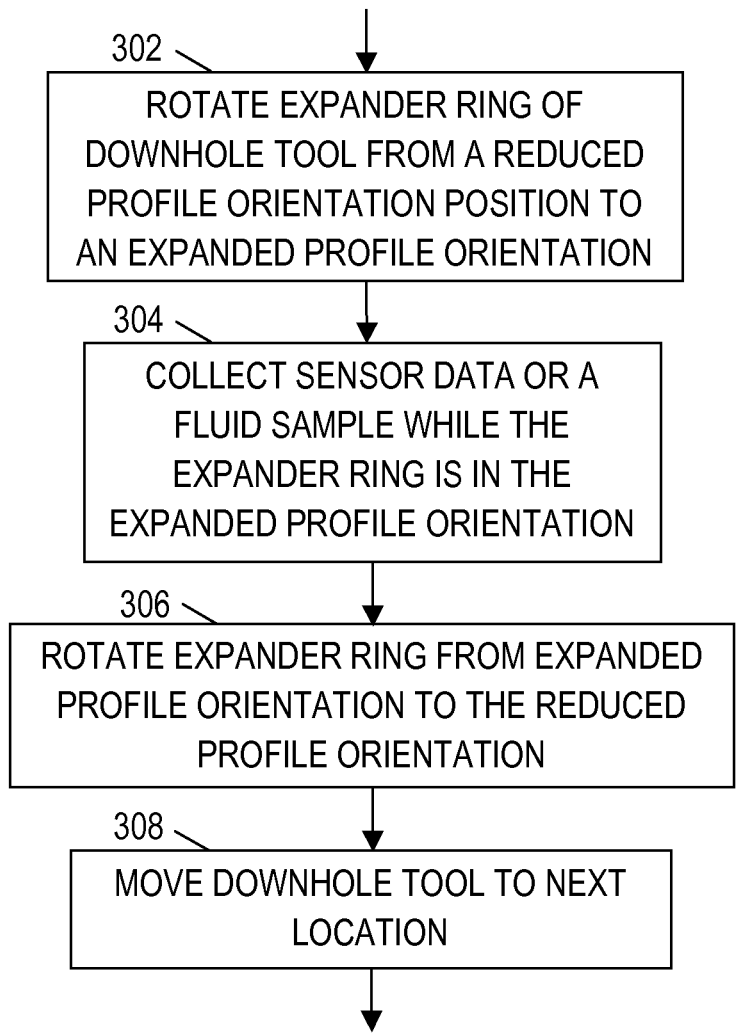
FIG. 10 shows an illustrative method for using a downhole tool with an expander ring.

FIG. 10 shows an illustrative method 300 for a downhole tool with an expander ring. As shown, the method 300 includes rotating an expander ring from a reduced profile orientation to an expanded profile orientation (see block 302). In some embodiments, the expander ring contacts or is proximate to opposite sides of a borehole wall while in its expanded profile orientation. Alternatively, a tool body of the downhole tool may contact or move proximate to the borehole wall when the expander ring is in its expanded profile orientation. At block 304, sensor data or a fluid sample is collected while the expander ring is in the expanded profile orientation. In some embodiments, the step of block 304 may involve receiving a fluid sample via a fluid sample interface integrated with the expander ring, or collecting a sensor measurement from a sensor integrated with the expander ring. At block 306, the expander ring is rotated from the expanded profile orientation to the reduced profile orientation. At block 308, the downhole tool is moved to a next position. The method 300 may be repeated as needed.

Numerous other variations and modifications will become apparent to those skilled in the art once the above disclosure is fully appreciated. It is intended that the following claims be interpreted to embrace all such variations and modifications where applicable.

What is claimed is:

1. A downhole tool, comprising:
   a tool body defining a tool centerline, and a recessed ring guide intermediate to ends of the tool body;
   an expander ring having an asymmetric wall thickness and rotatable around the recessed ring guide between a reduced tool profile orientation and an expanded tool profile orientation; and
   an actuator configured to rotate the expander ring between the reduced tool profile orientation and the expanded tool profile orientation.

2. The downhole tool of claim 1, wherein the entire expander ring projects beyond a profile of the tool body when in the expanded profile orientation.

3. The downhole tool of claim 1, wherein the expander ring is fully within the recessed ring guide when in the reduced profile orientation.

4. The downhole tool of claim 1, wherein the expander ring in the expanded profile orientation contacts or moves within a threshold proximity to a borehole wall on only one side of the tool.

5. The downhole tool of claim 1, wherein the expander ring in the expanded profile orientation contacts or moves within a threshold proximity to a borehole wall on opposite sides of the tool.

6. The downhole tool of claim 1, wherein the expander ring has a shape corresponding to a transverse slice of a cylinder with a hole that is perpendicular to the slice.

7. The downhole tool of claim 1, wherein the expander ring has a shape corresponding to a slice of a cylinder with a hole that is offset relative to the tool centerline.

8. The downhole tool of claim 1, wherein the expander ring comprises has a shape corresponding to a slice of a cylinder with a hole and with at least one extension member.

9. The downhole tool of claim 1, wherein the expander ring comprises a plurality of surfaces, and wherein at least one of the surfaces has elastomer wipers.

10. The downhole tool of claim 1, wherein the expander ring in the second profile orientation positions a fluid sampling interface or sensor within a threshold proximity to the borehole wall.

11. The downhole tool of claim 10, wherein the sensor is selected from a group consisting of a seismic sensor, a resistivity sensor, a gamma ray sensor, and a neutron porosity sensor.

12. The downhole tool of claim 1, further comprising a fluid sampling interface or sensor integrated with the expander ring.

13. The downhole tool of claim 1, further comprising a fluid sampling interface or sensor that aligns with an outer surface of the tool body, wherein the fluid sampling interface or sensor moves to within a threshold proximity of the borehole wall when the expander ring is in the expanded profile orientation.

14. The downhole tool of claim 1, wherein the downhole tool is part of a drill string and wherein the expander ring rotates from the expanded profile orientation to the reduced profile orientation by contacting the borehole wall during drilling.

15. The downhole tool of claim 1, further comprising at least one additional expander ring with a different reduced and expanded profile orientation.

16. A method for a downhole tool, comprising:
   rotating an expander ring around a recessed ring guide between a reduced profile orientation and an expanded profile orientation,
   collecting sensor data or a fluid sample while the expander ring is in the expanded profile orientation; and
   rotating the expander ring from the expanded profile orientation to the reduced profile orientation after said collecting.

17. The method of claim 16, further comprising projecting beyond a profile of the tool body on opposite sides when the expander ring is in the expanded profile orientation.

18. The method of claim 16, wherein further comprising moving the downhole tool closer to the borehole wall by rotating the expander ring to the expanded profile orientation.

19. The method of claim 16, wherein said collecting sensor data or a fluid sample is performed by a sensor or fluid sample interface integrated with the expander ring.

20. The method of claim 16, further comprising determining a borehole diameter while the expander ring is in the expanded profile orientation, and using the determined borehole diameter to adjust a sensor measurement.

* * * * *